(12) United States Patent
Seekamp et al.

(10) Patent No.: US 11,714,072 B2
(45) Date of Patent: Aug. 1, 2023

(54) REAGENT COMPOSITIONS AND METHOD FOR KARL FISCHER TITRATION

(71) Applicant: HONEYWELL INTERNATIONAL INC., Morris Plains, NJ (US)

(72) Inventors: Stefan Seekamp, Seelze (DE); Marco Konopatzki, Seelze (DE)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 471 days.

(21) Appl. No.: 16/827,163

(22) Filed: Mar. 23, 2020

(65) Prior Publication Data

US 2020/0309750 A1    Oct. 1, 2020

Related U.S. Application Data

(60) Provisional application No. 62/825,478, filed on Mar. 28, 2019.

(51) Int. Cl.
| | | |
|---|---|---|
| *G01N 31/16* | (2006.01) | |
| *C07D 207/16* | (2006.01) | |
| *C07D 233/56* | (2006.01) | |
| *C01B 17/48* | (2006.01) | |

(52) U.S. Cl.
CPC ........... *G01N 31/168* (2013.01); *C01B 17/48* (2013.01); *C07D 207/16* (2013.01); *C07D 233/56* (2013.01)

(58) Field of Classification Search
CPC .. G01N 31/168; C07D 233/56; C07D 207/16; C01B 17/48

USPC ........................................................... 436/42
See application file for complete search history.

(56) References Cited

U.S. PATENT DOCUMENTS

| | | |
|---|---|---|
| 5,102,804 A | 4/1992 | Fischer et al. |
| 5,139,955 A | 8/1992 | Scholz |
| 6,946,298 B2 | 9/2005 | Hoffmann et al. |
| 7,247,485 B1 | 7/2007 | Cedergren et al. |
| 2002/0127726 A1 | 9/2002 | Hoffmann et al. |

FOREIGN PATENT DOCUMENTS

| | | |
|---|---|---|
| DE | 3923883 A1 | 1/1991 |
| JP | 2007278919 A | 10/2007 |

*Primary Examiner* — Jeffrey H Murray
(74) *Attorney, Agent, or Firm* — Lorenz & Kopf, LLP

(57) ABSTRACT

A reagent composition for a Karl Fischer titration includes (1) sulfur dioxide or a derivative thereof, (2) a derivative of imidazole, (3) an alcohol, and (4) at least one amino acid that is present in an amount that is greater than zero and up to about 10 weight percent based on a total weight of the reagent composition. Moreover, a molar ratio of the derivative of imidazole to the sulfur dioxide or derivative thereof is greater than 1:1. Iodine is optionally included in a one-component reagent and excluded in a two-component reagent. This disclosure further provides a method for determining an amount of water in a sample via Karl Fischer titration. The method includes the step of providing the sample, providing the reagent composition, which optionally includes the iodine ($I_2$), and titrating the sample with the reagent composition.

20 Claims, No Drawings

REAGENT COMPOSITIONS AND METHOD FOR KARL FISCHER TITRATION

CROSS-REFERENCE TO RELATED APPLICATIONS

This application claims the benefit of U.S. Provisional Application No. 62/825,478, filed Mar. 28, 2019, which is expressly incorporated herein by reference in its entirety.

TECHNICAL FIELD

The present disclosure generally relates to both a one- and a two-component reagent composition for Karl Fischer titrations and methods of determining an amount of water in a sample using the reagent compositions. The present disclosure more specifically relates to use of a derivative of imidazole and an amino acid in the reagent composition.

BACKGROUND

The determination of water according to the Karl Fischer method, i.e., via Karl Fischer titration, utilizes the following reactions:

(1)

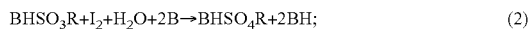
(2)

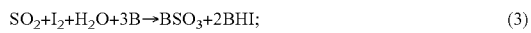
(3)

(4)

wherein B is a base and ROH is an alcohol. This titration is carried out in two basic forms, namely as a volumetric titration and as a coulometric titration.

In the classic Karl Fischer titration, a reagent includes an alkyl sulfite, which is oxidized to form an alkyl sulfate in the presence of water. Karl Fischer titrations are typically carried out in an alcoholic solution (such as methanol) or in the presence of the stoichiometric or a minimum amount of alcohol. The use of alcohols stabilizes the stoichiometry of the Karl Fischer reaction wherein the ratio of reacted iodine to water is 1:1.

The use of reagents which include $SO_2$ and pyridine has also been described wherein pyridine is used in excess. However, because of its weak basicity, pyridine cannot completely neutralize the alkyl-sulfurous acid intermediates described above. As a result, the reaction is slow, does not go to completion, and the end point is not stable. Because of this lack of stability, the repeatability of the results is often very poor. In addition, pyridine has a noxious odor. Moreover, in such systems, the determinable water equivalent is heavily dependent on experimental conditions. For example, in such systems, a pyridine-$SO_3$ adduct forms, which takes part in a water-consuming side reaction (reaction (4)) that can falsify the titration results.

Pyridine has since been with a stronger base with a higher affinity for alkylsulfites. For example, imidazole was found to have even more benefits than pyridine besides not having the noxious odor. Imidazole allows the reaction to go to completion rapidly and provides a stable end point. Later, researchers found that adding a second base, 2-methylimidazole, to the imidazole, enhances stability and reduces the appearance of undesired crystallization. However, toxicity concerns remain. Accordingly, there remains an opportunity to develop an improved Karl-Fischer reagent.

BRIEF SUMMARY

This disclosure provides a reagent composition for a two-component Karl Fischer titration. The reagent composition includes (1) sulfur dioxide or a derivative thereof and (2) a derivative of imidazole having the following structure:

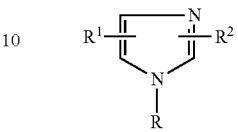

wherein each of R, $R^1$, and $R^2$ is independently a hydrogen atom, a phenyl group, a substituted phenyl group, a first hydrocarbyl group having from 1 to 6 carbon atoms, or a second hydrocarbyl group having 1 to 6 carbon atoms interrupted in at least one position with a heteroatom, provided that R, $R^1$, and $R^2$ are not all hydrogen atoms. The reagent composition also includes (3) an alcohol and (4) at least one amino acid that is present in an amount that is greater than zero and up to about 10 weight percent based on a total weight of the reagent composition. Moreover, a molar ratio of the derivative of imidazole to the sulfur dioxide or derivative thereof is greater than 1:1.

This disclosure also provides a reagent for a one-component Karl Fischer titration. This reagent composition includes the (1) sulfur dioxide or a derivative thereof, (2) the derivative of imidazole, (3) the alcohol, (4) the at least one amino acid, and (5) iodine ($I_2$).

This disclosure further provides a method for determining an amount of water in a sample via Karl Fischer titration. The method includes the step of providing the sample, providing the reagent composition, which optionally includes the iodine ($I_2$), and titrating the sample with the reagent composition to determine the amount of water therein.

Inclusion of the at least one amino acid decreases the standard deviation of titration measurements, thereby making the titration measurements, and determination of the amount of water, more accurate. In addition, inclusion of the at least one amino acid decreases the time needed to perform the titration. Moreover, the reagent composition of this disclosure is typically free of CMR substances which are substances that are carcinogenic, mutagenic or toxic to reproduction (CMR), as defined by various governmental or private agencies, as is known in the art. This increases the safety and usability of the reagent composition in various environments.

DETAILED DESCRIPTION

The following detailed description is merely exemplary in nature and is not intended to limit the method or reagent. Furthermore, there is no intention to be bound by any theory presented in the preceding background or the following detailed description.

Embodiments of the present disclosure are generally directed to methods of titration and compositions for the same. For the sake of brevity, conventional techniques may not be described in detail herein. Moreover, the various tasks and process steps described herein may be incorporated into a more comprehensive procedure or process having additional steps or functionality not described in detail herein. In particular, various steps in titrations are well-known and so, in the interest of brevity, many conventional steps will only be mentioned briefly herein or will be omitted entirely without providing the well-known process details. Various desirable features and characteristics of the present disclosure will become apparent from the subsequent detailed description of the disclosure and the appended claims, taken in conjunction with the accompanying drawings and the background of the disclosure.

This disclosure provides a reagent composition for a two-component Karl Fischer titration and a reagent composition for a one-component Karl Fisher titration. In other words, the reagent composition for the two-component titration is a single composition or solution that typically does not include a source of iodine ($I_2$), as is understood in the art. If iodine is required when using such a two-component composition, then it is added as the second component of the two component titration. The reagent composition for the one-component titration is also a single composition and typically includes the source of iodine. In this composition, an independent source of iodine is not typically required such that there is no second component needed. Therefore, such a composition and titration is typically described as one-component.

In one embodiment, a reagent composition for a two-component Karl Fischer titration includes (1) sulfur dioxide or a derivative thereof and (2) a derivative of imidazole having the following structure:

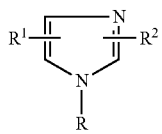

wherein each of R, $R^1$, and $R^2$ is independently a hydrogen atom, a phenyl group, a substituted phenyl group, a first hydrocarbyl group having from 1 to 6 carbon atoms, or a second hydrocarbyl group having 1 to 6 carbon atoms interrupted in at least one position with a heteroatom, provided that R, $R^1$, and $R^2$ are not all hydrogen atoms. This reagent composition also includes (3) an alcohol; and (4) at least one amino acid that is present in an amount that is greater than zero and up to about 10 weight percent based on a total weight of said reagent composition. Moreover, a molar ratio of the derivative of imidazole to the sulfur dioxide or derivative thereof is greater than 1:1. Typically, in such an embodiment, the reagent composition is free of iodine ($I_2$).

This disclosure also provides a reagent composition for a one-component Karl Fischer titration. This reagent composition includes the (1) sulfur dioxide or a derivative thereof, (2) the derivative of imidazole as described above, (3) the alcohol, (4) the at least one amino acid, and (5) iodine ($I_2$).

This disclosure further provides a method for determining an amount of water in a sample via Karl Fischer titration. The method includes the step of providing the aforementioned reagent composition, which optionally includes the iodine ($I_2$), and titrating the sample with the reagent composition. Typically, this method can be described as a version or variant of the Karl Fisher Titration that is used to determine an amount of water or moisture in a sample.

Each of the above is described in greater detail below.

Types of Karl Fischer Titration:

There are generally two methods used to perform the Karl Fischer titration. The first is known as a volumetric Karl Fischer titration. In this titration, the determination of the amount of water in the sample is based on an amount, or volume, of reagent used to convert the water. In this titration, samples are dissolved in a solvent before the titration begins. A reagent is added until the water is removed.

The second method is known as a coulometric Karl Fischer titration. In this titration, a reagent and solvent are combined in a titration cell. When a sample is introduced into the titration cell and dissolved, reagent is released by the induction of an electrical current. The amount of current required to convert the water is determinant of the amount of water in the sample. An advantage of the coulometric Karl Fischer titration is the capability to accurately measure small amounts of water, e.g. as low as 0.1 microgram (μg) of water. Each titration is described in greater detail below.

Reagent Composition:

The method includes the step of providing the reagent composition. The terminology "reagent" and "reagent composition" may be alternatively used below and both refer to the reagent composition of this disclosure. The reagent composition may be alternatively described as a "Karl Fischer reagent." The reagent composition may be a one component reagent composition or a two component reagent composition. The reagent composition is used in titrating the sample that includes the amount of water therein. For example, the reagent composition can be used in either Karl Fischer method described above, e.g. volumetric or coulometric titrations. The regent composition may be described as a titrating solution, e.g. when used in coulometric titrations. In volumetric titrations, e.g. in one or two component reagent compositions, the reagent composition of this disclosure may act as a solvent and may include solvent, such as the alcohol, therein.

In one embodiment, the reagent composition includes (1) sulfur dioxide or a derivative thereof, (2) a derivative of imidazole, (3) an alcohol, and (4) at least one amino acid that is present in an amount that is greater than zero and up to about 10 weight percent based on a total weight of the reagent composition. Moreover, a molar ratio of the derivative of imidazole to the sulfur dioxide or derivative thereof is greater than 1:1. In another embodiment, the reagent composition includes the aforementioned components (1)-(4) and iodine ($I_2$). The reagent may be, consist essentially of, or consist of, the aforementioned compounds.

The terminology "consisting essentially of" may describe embodiments that are free of, one or more amines, such as those having a pKA of more than 6, for example, an optionally substituted aliphatic, cyclic, heterocyclic or aromatic amines such as pyridine and derivatives thereof, trialkylamines, such as trimethylamine, triethylamine, tri-n-propylamine, tri-n-butylamine, N,N-dimethylethylamine, N,N-diethylmethylamine, N,N-dimethyl-n-butylamine, also N,N,N',N'-tetramethylethylenediamine, imidazole, 1-methylpiperidine, 1-ethylpiperidine, 1,2-dimethylpyrrolidine, 1-methylpyrrolidine, N-ethylmorpholine, N-methylmorpholine, and combinations thereof.

The terminology "consisting essentially of" may alternatively describe embodiments that are free of one or more soluble iodides such as sodium iodide, or iodides of organic cations, such as tetrabutylammonium iodide, imidazole hydrogen iodide or trimethylamine hydrogen iodide and/or dissociating organic salts such as, for example, tetrabutylammonium chloride, diethanolamine hydrogen bromide, guanidinium salts such as guanidinium benzoate, and/or combinations thereof. The reagent composition may include, or be free of, imidazole itself. The reagent may also include, or be free of, nitrogen bases such as salts or carboxylic acids, such as tetramethylammonium acetate, trimethylammonium acetate, tetrabutylammonium benzoate, lithium propionate acetic acid, propionic acid, butyric acid, benzoic acid, buffer substances such diethanolammonium benzoate or imidazolium acetate, or combinations thereof.

The terminology "consisting essentially of" may alternatively describe embodiments that are free of derivatives of sulfur dioxide, or free of sulfur dioxide, or free of imidazole, or free of a hydroiodide of a derivative of imidazole such as a hydroiodide of any derivative of imidazole contemplated herein, etc.

The reagent composition may also be free of, an aprotic solvent, including, but not limited to, ethers, such as diisopropyl ether, dibutyl ether, dioxane, tetrahydrofuran, nitriles, such as acetonitrile, esters, such as ethyl acetate, ethyl propionate, isobutyl acetate, n-butyl acetate, ethylene carbonate, propylene carbonate, butyrolactone, halogenated hydrocarbons, such as chloroform, carbon tetrachloride, 1,2-dichloropropane, methylene chloride, acid amides, such as dimethylformamide, dimethylacetamide, N-methylpyrrolidone, ketones, such as acetone, methyl ethyl ketone, diethyl ketone, cyclohexanone, methylcyclohexanone, ethylene carbonate, acetylacetone and other aprotic solvents, such as, for example, dimethylacetal. In one embodiment, the aprotic solvent is chosen from acetonitrile, propylene carbonate, ethyl acetate, tetrahydrofuran, dioxane, dimethylformamide or methylene chloride and combinations thereof. In a further embodiment, the aprotic solvent is chosen from cyclic and non-cyclic carbonates, ethers, esters, halo-hydrocarbons, acid amides, nitriles, ketones, glycol ethers, and combinations thereof. In another embodiment, the aprotic solvent is chosen from acetonitrile, ethylene carbonate, propylene carbonate, and combinations thereof. In another embodiment, the aprotic solvent is chosen from acetonitrile, propylene carbonate, and combinations thereof. In one embodiment, the aprotic solvent is acetonitrile. In another embodiment, the aprotic solvent is propylene carbonate. In still other embodiments, the aprotic solvent may be pure (liquid) derivatives of imidazole, such as any described herein. It is contemplated that the reagent composition may be free of one or more of the aforementioned aprotic solvents or may include less than 5, 4, 3, 2, 1, 0.5, or 0.1, weight percent of one or more of the aforementioned aprotic solvents based on a total weight of the reagent. In various non-limiting embodiments, it is also contemplated that all values and ranges of values between and including those values set forth above are expressly contemplated for use herein.

The reagent composition may also be free of substituted aliphatic, cyclic, heterocyclic or aromatic amines such as pyridine and derivatives thereof, trialkylamines, such as trimethylamine, triethylamine, tri-n-butylamine, N,N-dimethylethylamine, N,N-diethylmethylamine, imidazole, N-ethylmorpholine, N-methylmorpholine, 1-methylpiperidine, 1-ethylpiperidine, 1-methylpyrrolidine, and combinations thereof.

The terminology "free of", throughout this specification, can describe less than 5, 4, 3, 2, 1, 0.5, or 0.1, weight percent of the compound based on a total weight of the reagent composition. Alternatively, "free of" may refer to an amount of zero weight percent, i.e., totally free, of the compound.

Sulfur Dioxide/Derivative of Sulfur Dioxide

Referring back, the sulfur dioxide is known in the art to be $SO_2$. The terminology "derivative thereof" describes compounds that act the same or substantially similarly to sulfur dioxide in the Karl-Fischer titration, as would be understood by one of skill in the art. For example, derivatives that may be used include, but are not limited to, reducing agents, sulfites such as dimethylsulfite, diethylsulfite, and combinations thereof.

In one additional embodiment, the sulfur dioxide or derivative thereof is present in an amount of from about 0.05 to about 5, mols/liter of the reagent. In other embodiments, the sulfur dioxide or derivative thereof is present in an amount of from about 0.05 to about 1, from about 0.1 to about 1, or from about 0.1 to about 0.5, mols/liter of the reagent. In other embodiments, the sulfur dioxide or derivative thereof present in an amount of from about 6 to about 10, e.g. about 6, 7, 8, 9, or 10, weight percent based on a total weight of said reagent composition. In various non-limiting embodiments, it is also contemplated that all values and ranges of values between and including those values set forth above are expressly contemplated for use herein.

Derivative of Imidazole:

The derivative of imidazole has the following structure:

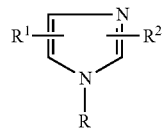

wherein each of R, $R^1$, and $R^2$ is independently a hydrogen atom, a phenyl group, a substituted phenyl group, a first hydrocarbyl group having from 1 to 6 carbon atoms, or a second hydrocarbyl group having 1 to 6 carbon atoms interrupted in at least one position with a heteroatom. In this structure, R, $R^1$, and $R^2$ cannot all be hydrogen atoms because then the structure would be imidazole itself. In various embodiments, the first hydrocarbyl group has 1, 2, 3, 4, 5, or 6 carbon atoms. The second hydrocarbyl group may also independently include 1, 2, 3, 4, 5, or 6 carbon atoms wherein at one or more points in the chain of the group, a heteroatom including, but not limited to, nitrogen, oxygen, phosphorous, chlorine, bromine, or iodine. Moreover, each of $R^1$ and $R^2$ may be located at any point on the ring. In one additional embodiment, each of R, $R^1$, and $R^2$ is independently a hydrogen atom or a methyl, ethyl, or butyl group, provided that R, $R^1$, and $R^2$ are not all hydrogen atoms. In one embodiment, the derivative of imidazole is 2-ethylimidazole.

In various embodiments, the derivative of imidazole is present in the reagent composition in the amounts set forth above relative to the sulfur dioxide or derivative thereof. In other embodiments, the derivative of imidazole is present in an amount of from about 0.5 to about 5.5, or about 0.5 to about 5, or about 0.5 to about 2.5, mols/liter of the reagent. In other embodiments, the derivative of imidazole is present is present in an amount that reflects one or more of the aforementioned molar ratios of the derivative of imidazole to the sulfur dioxide or derivative thereof of greater than 1:1. For example, whatever the number of moles of the sulfur dioxide or derivative thereof is in the reagent, the derivative of imidazole may be present in a number of moles that is greater than 1:1, e.g. in any of the ratios set forth above or when used in excess, e.g. as solvent. In various non-limiting embodiments, it is also contemplated that all values and ranges of values between and including those values set forth above are expressly contemplated for use herein.

Molar Ratio of the Derivative of Imidazole to the Sulfur Dioxide or Derivative Thereof:

The reagent composition typically includes a molar ratio of the derivative of imidazole to the sulfur dioxide or derivative thereof that is greater than 1:1. In other words, this disclosure does not utilize a 1:1 molar ratio of the derivative of imidazole to the sulfur dioxide or derivative thereof. In various embodiments, the molar ratio of the derivative of imidazole to the sulfur dioxide or derivative thereof is about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, about 10:1, about 10.5:1, about 11:1, about 11.5:1, about 12:1, about 12.5:1, about 13:1, about 13.5:1, about 14:1, about 14.5:1, about 15:1, about 15.5:1, about 16:1, about 16.5:1, about 17:1, about 17.5:1, about 18:1, about 18.5:1, about 19:1, about 19.5:1, or about 20:1. In various embodiments, if a liquid imidazole derivative is used, then the molar ratio can be much higher than 20:1, e.g. 30:1, 40:1, 50:1, or even higher. In one embodiment, the molar ratio of the derivative of imidazole to the sulfur dioxide or derivative thereof is greater than 2:1. In another embodiment, the molar ratio of the derivative of imidazole to the sulfur dioxide or derivative thereof is greater than 5:1. In a further embodiment, the molar ratio of the derivative of imidazole to the sulfur dioxide or derivative thereof is about 14:1. Moreover, it is contemplated that the reagent composition may include amounts "greater than" any of the aforementioned ratios, e.g., "greater than" about 2:1, greater than about 2.5:1, etc. In various non-limiting embodiments, it is also contemplated that all values and ranges of values between and including those values set forth above are expressly contemplated for use herein.

Alcohol:

The reagent composition also includes an alcohol. Water determination using a Karl Fischer process poses no problems for most alcohols. Alcohols are easily soluble in the common Karl Fischer working media. Only alcohols with very long chains require the addition of solubilizers. Side reactions are not to be expected. Accordingly, any alcohol known in the art of Karl Fischer titrations can be used herein. Typically, the alcohol is methanol, ethanol, or a combination thereof. Alternatively, the alcohol may be any length alkyl alcohol, i.e., R—OH wherein R is an alkyl group having, for example, 1 to 10, 2 to 9, 3 to 8, 4 to 7, or 5 or 6, carbon atoms in a linear, branched, or cyclic group. In various non-limiting embodiments, it is also contemplated that all values and ranges of values between and including those values set forth above are expressly contemplated for use herein.

The amount of alcohol is not particularly limited and may be present in an amount of from about 60 to about 80, about 65 to about 75, about 75 to about 80, about 70 to about 80, about 60 to about 70, or about 65 to about 70, weight percent based on a total weight of the composition. In various non-limiting embodiments, it is also contemplated that all values and ranges of values between and including those values set forth above are expressly contemplated for use herein.

At Least One Amino Acid:

The composition also includes at least one amino acid, e.g. as a titration additive. The terminology "at least one" means that one or more than one amino acid can be used. For example, a combination of two or more amino acids can be used. The amino acid is not particularly limited and may be any known in the art. The terminology "amino acid" typically describes organic compounds that include amine (—NH2) and carboxyl (—COOH) functional groups, along with a side chain (R group) specific to each amino acid. As is known in the art, there are about 500 naturally occurring amino acids are known. These amino acids can be classified according to the core structural functional groups' locations as alpha- ($\alpha$-), beta- ($\beta$-), gamma- ($\gamma$-) or delta- ($\delta$-) amino acids. They can alternatively be described relative to polarity, pH level, and side chain group type (aliphatic, acyclic, aromatic, containing hydroxyl or sulfur, etc.). The at least one amino acid can be present in the "L" or "D" forms or as a mixture in both forms.

In various embodiments, the at least one amino acid of this disclosure is proline. Proline is a proteinogenic amino acid that includes an $\alpha$-amino group, an $\alpha$-carboxylic acid group, and a side chain pyrrolidine, classifying it as a nonpolar (at physiological pH), aliphatic amino acid. Alternatively, derivatives of proline may also be used. These may be any known in the art, including, but not limited to, hydroxy proline, alkylated proline wherein the alkyl group may have, for example, 1 to 10, 2 to 9, 3 to 8, 4 to 7, or 5 or 6, carbon atoms in a linear, branched, or cyclic group. Moreover, the hydroxy and/or alkyl groups may be present at any atom in proline, i.e., at any position. In other embodiments, derivatives of proline that may be used include alkylated prolines (such as methylated proline), benzyl prolines, hydroxy prolines, etc. The at least one amino acid may be or consist of proline and/or any derivative thereof. In various non-limiting embodiments, it is also contemplated that all values and ranges of values between and including those values set forth above are expressly contemplated for use herein.

The at least one amino acid is typically present in the reagent composition in any amount of from greater than zero up to about 10 wt %, based on a total weight of the reagent composition. The terminology "in any amount of from greater than zero" typically means any positive amount, e.g. about 0.001, about 0.005, about 0.01, about 0.05, about 0.1, about 0.5, or greater weight percent, based on a total weight of the reagent composition. In other embodiments, the at least one amino acid is present in an amount of from about 0.1 to about 2, about 1 to about 2, about 1 to about 5, about 5 to about 10, about 0.1 to about 1, about 0.1 to about 0.5, about 0.2 to about 0.5, about 0.2 to about 0.4, about 0.2 to about 0.3, about 0.3 to about 0.4, about 0.3 to about 0.5, about 0.4 to about 0.5, etc. weight percent based on a total weight of the composition. In one embodiment, the at least one amino acid is present in an amount of greater than zero and up to about 5, 7.5, 10, 12.5, or even 15, weight percent based on a total weight of the reagent composition. For example, the amino acid may be present in an amount of up to about 15 weight percent, e.g. when used in methanol. In various non-limiting embodiments, it is also contemplated that all values and ranges of values between and including those values set forth above are expressly contemplated for use herein.

CMR Substances

Typically, the reagent composition of this disclosure is free of CMR substances which are substances that are carcinogenic, mutagenic or toxic to reproduction (CMR), as defined by various governmental or private agencies. The Globally Harmonized System (GHS), which is a framework from which competent authorities may select the appropriate harmonized classification & communication elements, can be used to determine the nature and the relative severity of the hazard of a chemical substance or a mixture. Accordingly, in various embodiments, the reagent composition is free of one or more CMR substances that are categorized by GHS in Category 1A: Known human carcinogen (H340), mutagen (H350) or reproductive toxicant (H360) based on human evidence; Category 1B: Presumed human carcinogen (H340), mutagen (H350) or reproductive toxicant (H360) based on animal studies; and/or Category 2: Suspected carcinogen (H341), mutagen (H351) or reproductive toxicant (H361) based on limited evidence from animal studies or/and human. For example, the reagent composition is typically free of imidazole. The terminology "free of", throughout this specification, can describe less than 5, 4, 3, 2, 1, 0.5, or 0.1, weight percent of the CMR substance based on a total weight of the reagent composition. Alternatively, "free of" may refer to an amount of zero weight percent in the reagent composition, i.e., totally free, of the CMR substance. In various non-limiting embodiments, it is also contemplated that all values and ranges of values between and including those values set forth above are expressly contemplated for use herein.

Additional Embodiments of the Reagent Composition:

In one embodiment, the sulfur dioxide or derivative thereof is present in an amount of from about 0.05 to about 1, mols/liter of the reagent composition, the derivative of imidazole is 2-ethylimidazole and is present is present in an amount of from about 0.5 to about 5, mols/liter of the reagent composition, the at least one amino acid is present in an amount of from greater than zero and up to about 5, 7.5, 10, 12.5, or 15, weight percent based on a total weight of the reagent composition, and the alcohol is methanol and/or ethanol. For example, the at least one amino acid can be proline. In similar embodiments, the at least one amino acid is present in an amount of from about 0.1 to about 0.5, about 0.2 to about 0.5, about 0.2 to about 0.4, about 0.2 to about 0.3, about 0.3 to about 0.4, about 0.3 to about 0.5, about 0.4 to about 0.5, etc. weight percent based on a total weight of the composition. In various non-limiting embodiments, it is also contemplated that all values and ranges of values between and including those values set forth above are expressly contemplated for use herein.

In another embodiment, the sulfur dioxide or derivative thereof is present in an amount of from about 0.05 to about 1, mols/liter of the reagent composition, the derivative of imidazole is 2-ethylimidazole and is present is present in an amount of from about 0.5 to about 5, mols/liter of the reagent composition, the at least one amino acid is present in an amount of from about 0.1 to about 2 weight percent based on a total weight of the reagent composition, and the alcohol is methanol and/or ethanol. Again, the at least one amino acid can be proline. In similar embodiments, the at least one amino acid is present in an amount of from about 0.1 to about 0.5, about 0.2 to about 0.5, about 0.2 to about 0.4, about 0.2 to about 0.3, about 0.3 to about 0.4, about 0.3 to about 0.5, about 0.4 to about 0.5, etc. weight percent based on a total weight of the composition. In various non-limiting embodiments, it is also contemplated that all values and ranges of values between and including those values set forth above are expressly contemplated for use herein.

In still another embodiment, the reagent composition consists of the sulfur dioxide or derivative thereof which is present in an amount of from about 0.05 to about 1, mols/liter of the reagent composition, the derivative of imidazole is 2-ethylimidazole and is present is present in an amount of from about 0.5 to about 5, mols/liter of the reagent composition, the at least one amino acid is proline and is present in an amount of greater than zero up to about 5, 7.5, 10, 12.5, or 15, weight percent based on a total weight of the reagent composition, and the alcohol is methanol and/or ethanol. In similar embodiments, the at least one amino acid is present in an amount of from about 0.1 to about 0.5, about 0.2 to about 0.5, about 0.2 to about 0.4, about 0.2 to about 0.3, about 0.3 to about 0.4, about 0.3 to about 0.5, about 0.4 to about 0.5, etc. weight percent based on a total weight of the composition. In various non-limiting embodiments, it is also contemplated that all values and ranges of values between and including those values set forth above are expressly contemplated for use herein.

In a further embodiment, the reagent composition consists of the sulfur dioxide or derivative thereof that is present in an amount of from about 0.05 to about 1, mols/liter of the reagent composition, the derivative of imidazole is 2-ethylimidazole and is present is present in an amount of from about 0.5 to about 5, mols/liter of the reagent composition, the at least one amino acid is proline and is present in an amount of from about 0.1 to about 2 weight percent based on a total weight of the reagent composition, and the alcohol is methanol and/or ethanol. In similar embodiments, the at least one amino acid is present in an amount of from about 0.1 to about 0.5, about 0.2 to about 0.5, about 0.2 to about 0.4, about 0.2 to about 0.3, about 0.3 to about 0.4, about 0.3 to about 0.5, about 0.4 to about 0.5, etc. weight percent based on a total weight of the composition. In various non-limiting embodiments, it is also contemplated that all values and ranges of values between and including those values set forth above are expressly contemplated for use herein.

In yet another embodiment, the reagent composition is for a one-component Karl Fischer titration. The reagent composition of this embodiment includes the sulfur dioxide or a derivative thereof, the derivative of imidazole as described above, the alcohol, the at least one amino acid, and iodine ($I_2$), wherein a molar ratio of the derivative of imidazole to the sulfur dioxide or derivative thereof is greater than 1:1. The iodine ($I_2$) is typically present in an amount as is described in detail below.

Method for Determining an Amount of Water in a Sample Via Karl Fischer Titration:

Referring back, this disclosure also provides the method for determining an amount of water in a sample via Karl Fischer titration. The method includes the steps of providing the sample, providing the aforementioned reagent composition, titrating the sample using the reagent composition.

Referring to the step of providing the sample, the sample may be provided in any form as is typically chosen by one of skill in the art. The sample may be any sort of sample that includes water. The amount of water in the sample is not particularly limited and may be chosen by one of skill in the art. For example, in coulometric titrations, the amount of water in the sample is typically from about 0.1 to about 3000 µg of water or from about 20 to about 3000 µg of water. In volumetric titrations, the amount of water can greatly exceed 3000 µg. In still other embodiments, the maximum amount of water is determined by the size of the vessel used because of the amount of the reagent that would be required. The sample may be a liquid, gas, or solid provided that the sample includes an amount of water therein. The sample is typically a liquid that includes an amount of water therein. Moreover, the sample may be provided in any amount that is typically chosen by one of skill in the art of titration. In various non-limiting embodiments, it is also contemplated that all values and ranges of values between and including those values set forth above are expressly contemplated for use herein.

Referring specifically to the step of providing the reagent composition, the reagent composition may be formed/provided using any order of addition. For example, any total amount or partial amount of any of the aforementioned components may be combined with any total amount or partial amount of any other of the components.

In one embodiment, the method includes the step of titrating the sample with the reagent composition. In one embodiment, this is described as a coulometric method. In another embodiment, this is described as a volumetric method. For example, the method may include the step of combining the sample and the reagent composition such that the sample can be titrated. In this embodiment, the method typically includes the step of providing a source of iodine ($I_2$). This is typically described as a volumetric method. The source of iodine may be any known in the art, e.g. solid $I_2$ dissolved in any suitable solvent. In various embodiments, the solution to which the iodine is added may have from about 1 to about 10 weight percent of iodine after its addition. In a coulometric method, the iodine can be generated by anodic oxidation of an iodide such that no additional or external source of iodine may be needed/used. The sample can be titrated to determine the amount of water in the sample by using one of the aforementioned Karl Fischer methods. In various non-limiting embodiments, it is also contemplated that all values and ranges of values between and including those values set forth above are expressly contemplated for use herein.

For example, any necessary iodine can be added or can be generated by anodic oxidation from added iodide. During method, the added or anodically generated iodine is typically reduced to iodide by the reaction with the sulfur dioxide or derivative thereof and water. When there is no more water, free iodine is left over. The iodine excess can be used for indicating the end-point, for example for visual or for photometric indication. It is also possible to indicate the end-point electrochemically, for example bipotentiometrically or biamperometrically.

Volumetric determination can be carried out by introducing the reagent composition into the titration vessel as a solvent component. Then the sample can be added to the titration vessel such that the water is titrated by introducing an iodine containing one-component reagent composition or a two-component reagent composition of this disclosure. Typically, titrations utilizing a one-component reagent composition that is traditionally a solution of iodine, base and SO2 include providing a solvent in a vessel, adding the sample to the vessel that includes the solvent, and then adding the one-component reagent composition to the combination of the sample in the vessel and the solvent. The reagent composition of this disclosure can be used in this titration as a solvent. Titrations utilizing a two-component reagent composition typically include providing, e.g. a base and SO2 containing solvent like the reagent composition of this disclosure in a vessel. Then a sample is typically added to the vessel. Finally, the two-component reagent composition is then typically added to the vessel such that the titration reactions can begin.

Coulometric determination can be carried out, for example, by introducing the components of the reagent composition into a coulometric cell, such as a divided cell and then, according to the cell construction, adding the sample and electrolyzing, by switching on the electrolysis current, until the water present in the sample has been converted.

Prior to the determination of an amount of water in the sample, water contained in the alcohol can be removed in a blank titration (e.g. by pre-electrolysis in the case of a coulometric determination). In various embodiments, e.g. if the coulometric cell requires a reagent having a conductivity of from about 1 to about 10 mS/cm, it may be necessary to add additional supporting electrolytes. These may be soluble inorganic salts such as tetrabutylammonium chloride, imidazolium hydrogen bromide, etc.

To indicate the end-point, both in volumetric analysis and in coulometric titration, it is contemplated that bipotentiometric or biamperometric indication may be utilized. For example, the reagent composition and/or sample may be spiked with one or more known compounds that have known reproducible end-points. These may be chosen by those of skill in the art. Moreover, one or more buffers may be utilized.

EXAMPLES

A series of titrations are performed with a two-component system according to this disclosure and as comparative examples. Results are set forth below.

In a first series of examples, repeated titrations of an Hydranal Water Standard 10.0, #34849 having 10 mg/g water are completed. The base used is 2-ethylimidazole. The alcohol used is ethanol. 10 individual titrations are performed on a comparative example that does not include any amino acid. 10 individual titrations are also performed on an inventive example that include 0.23 wt % of proline as the amino acid. The standard deviations of both the comparative example and the inventive example are then calculated. As is shown below, the standard deviation of the inventive example is surprisingly superior to that of the comparative example. A Metrohm Titrando 888 with KF equipment was utilized, as known in the art. The titration type is volumetric. The amount of $SO_2$ present is about 8% (w/w).

|  | Comparative Example | Inventive Example |
|---|---|---|
| Derivative of Imidazole | 2-Ethylimidazole 17.6% (w/w) | 2-Ethylimidazole 17.6% (w/w) |
| Alcohol | Ethanol 74% (w/w) | Ethanol 74% (w/w) |
| Amino Acid | None | 0.23 wt % Proline |
| Titration 1 | 9.91 mg/g | 9.97 mg/g |
| Titration 2 | 9.98 mg/g | 9.99 mg/g |
| Titration 3 | 10 mg/g | 9.98 mg/g |
| Titration 4 | 10.02 mg/g | 9.99 mg/g |
| Titration 5 | 10.04 mg/g | 9.99 mg/g |
| Titration 6 | 9.94 mg/g | 9.96 mg/g |
| Titration 7 | 10.00 mg/g | 9.97 mg/g |
| Titration 8 | 10.02 mg/g | 9.99 mg/g |
| Titration 9 | 10.04 mg/g | 9.97 mg/g |
| Titration 10 | 10.04 mg/g | 10.00 mg/g |
| Standard deviation | 0.042 | 0.012 |

In a second series of examples, repeated titrations of a maleic acid standard for synthesis, Merck #8.00380 are completed. The base used is 2-ethylimidazole. The alcohol used is methanol. Four individual titrations (Titrations 1-4) are performed on a comparative example that does not include any amino acid. Five individual titrations (Titrations 5-9) are also performed on an inventive example that include 0.46 wt % of proline as the amino acid. The amount of time required to complete each titration is recorded and the standard deviation is calculated. As is shown below, the standard deviation of the inventive example is surprisingly superior to that of the comparative example. A Metrohm Titrando 888 with KF equipment was utilized, as known in the art. The titration type is volumetric. The amount of $SO_2$ present is about 8% (w/w).

| Water Determination in Maleic Acid at Detection Limit | | | | | |
|---|---|---|---|---|---|
| | Proline | Maleic Acid | Water (ppm) | Time (sec) | Standard Deviation | Avg. Time to Complete Titration |
| Comparative Examples | | | | | |
| Titration 1 | None | 5 g | 17 | 15 | | |
| Titration 2 | None | 10 g | 24 | 29 | | |
| Titration 3 | None | 15 g | 22 | 15 | | |
| Titration 4 | None | 20 g | 24 | 31 | 2.9 | 22.5 Seconds |
| Inventive Examples | | | | | |
| Titration 5 | 0.46% | 5 g | 21 | 16 | | |
| Titration 6 | 0.46% | 10 g | 20 | 16 | | |
| Titration 7 | 0.46% | 15 g | 24 | 18 | | |
| Titration 8 | 0.46% | 20 g | 26 | 27 | | |
| Titration 9 | 0.46% | 25 g | 24 | 22 | 2.2 | 19.8 Seconds |

Inclusion of the at least one amino acid decreases the standard deviation of titration measurements, thereby making the titration measurements, and determination of the amount of water, more accurate. In addition, inclusion of the at least one amino acid decreases the time needed to perform the titration. Moreover, the reagent composition of this disclosure is typically free of CMR substances which are substances that are carcinogenic, mutagenic or toxic to reproduction (CMR), as defined by various governmental or private agencies, as is known in the art. This increases the safety and usability of the reagent composition in various environments. While performing the experiments, it is observed that the composition of this disclosure has no tendency to crystallize at e.g. bottle edges. This can be beneficial in combination with the titration equipment.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

What is claimed is:

1. A reagent composition for a two-component Karl Fischer titration, said reagent composition comprising:
   (1) sulfur dioxide;
   (2) a derivative of imidazole having the following structure:

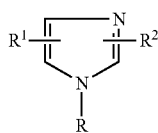

wherein each of R, $R^1$, and $R^2$ is independently a hydrogen atom or a hydrocarbyl group having from 1 to 6 carbon atoms, provided that R, $R^1$, and $R^2$ are not all hydrogen atoms;
   (3) an alcohol; and
   (4) at least one amino acid present in an amount from about 0.0001 to about 15 weight percent based on a total weight of said reagent composition;
   wherein a molar ratio of the derivative of imidazole to the sulfur dioxide is greater than 1:1.

2. The reagent composition of claim 1 wherein said at least one amino acid is proline.

3. The reagent composition of claim 2 wherein said proline is present in an amount from about 0.0001 to about 15 weight percent based on a total weight of said reagent composition.

4. The reagent composition of claim 2 wherein said proline is present in an amount of from about 0.1 to about 2 weight percent based on a total weight of said reagent composition.

5. The reagent composition of claim 2 wherein said proline is present in an amount of from about 0.2 to about 0.5 weight percent based on a total weight of said reagent composition.

6. The reagent composition of claim 1 wherein said sulfur dioxide is present in an amount of from about 0.05 to about 1, mols/liter of said reagent composition,
   said derivative of imidazole is 2-ethylimidazole and is present is present in an amount of from about 0.5 to about 5, mols/liter of said reagent composition,
   said at least one amino acid is present in an amount of from about 0.2 to about 0.5 weight percent based on a total weight of said reagent composition, and said alcohol is methanol and/or ethanol.

7. The reagent composition of claim 6 wherein said at least one amino acid is proline.

8. The reagent composition of claim 1 wherein said sulfur dioxide is present in an amount of from about 0.05 to about 1, mols/liter of said reagent composition,
   said derivative of imidazole is 2-ethylimidazole and is present is present in an amount of from about 0.5 to about 5, mols/liter of said reagent composition,
   said at least one amino acid is present in an amount of from about 0.1 to about 2 weight percent based on a total weight of said reagent composition, and
   said alcohol is methanol and/or ethanol.

9. The reagent composition of claim 8 wherein said at least one amino acid is proline.

10. The reagent composition of claim 1 consisting of:
    said sulfur dioxide present in an amount of from about 0.05 to about 1, mols/liter of said reagent composition,
    said derivative of imidazole that is 2-ethylimidazole and that is present is present in an amount of from about 0.5 to about 5, mols/liter of said reagent composition,
    said at least one amino acid that is proline and that is present in an amount of from about 0.2 to about 0.5 weight percent based on a total weight of said reagent composition, and said alcohol that is methanol and/or ethanol.

11. The reagent composition of claim 1 consisting of:
    said sulfur dioxide present in an amount of from about 6 to about 10, weight percent based on a total weight of said reagent composition;
    said derivative of imidazole that is 2-ethylimidazole and that is present is present in an amount of from about 17 to about 18 weight percent based on a total weight of said reagent composition,
    said at least one amino acid that is proline and that is present in an amount of from about 0.2 to about 0.5 weight percent based on a total weight of said reagent composition, and said alcohol that is ethanol and that is present in an amount of from about 70 to about 75 weight percent based on a total weight of said reagent composition.

12. A method for determining an amount of water in a sample via Karl Fischer titration, said method comprising the steps of:
A. providing the sample;
B. providing a reagent composition comprising:
(1) sulfur dioxide;
(2) a derivative of imidazole having the following structure:

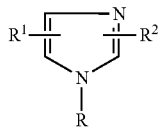

wherein each of R, $R^1$, and $R^2$ is independently a hydrogen atom or a hydrocarbyl group having from 1 to 6 carbon atoms, provided that R, $R^1$, and $R^2$ are not all hydrogen atoms;
(3) an alcohol;
(4) at least one amino acid present in an amount from about 0.0001 to about 15 weight percent based on a total weight of the reagent composition; and
(5) optionally iodine ($I_2$);
wherein a molar ratio of the derivative of imidazole to the sulfur dioxide is greater than 1:1; and
C. titrating the sample with the reagent composition.

13. The method of claim 12 wherein the at least one amino acid is proline.

14. The method of claim 13 wherein the proline is present in an amount of greater than zero and up to about 15 weight percent based on a total weight of the reagent composition.

15. The method of claim 13 wherein the proline is present in an amount of from about 0.2 to about 0.5 weight percent based on a total weight of the reagent composition.

16. The method of claim 12 wherein the sulfur dioxide or derivative thereof is present in an amount of from about 0.05 to about 1, mols/liter of the reagent composition,
the derivative of imidazole is 2-ethylimidazole and is present is present in an amount of from about 0.5 to about 5, mols/liter of the reagent composition, the at least one amino acid is proline and is present in an amount of from about 0.2 to about 0.5 weight percent based on a total weight of the reagent composition, and the alcohol is methanol and/or ethanol.

17. The method of claim 12 wherein the sulfur dioxide or derivative thereof is present in an amount of from about 0.05 to about 1, mols/liter of the reagent composition, the derivative of imidazole is 2-ethylimidazole and is present is present in an amount of from about 0.5 to about 5, mols/liter of the reagent composition,
the at least one amino acid is proline and is present in an amount of from about 0.1 to about 2 weight percent based on a total weight of the reagent composition, and the alcohol is methanol and/or ethanol.

18. (Withdrawn/Currently amended) A reagent composition for a one-component Karl Fischer titration, said reagent composition comprising:
(1) sulfur dioxide;
(2) a derivative of imidazole having the following structure:

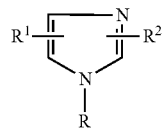

wherein each of R, $R^1$, and $R^2$ is independently a hydrogen atom or a hydrocarbyl group having from 1 to 6 carbon atoms, provided that R, $R^1$, and $R^2$ are not all hydrogen atoms;
(3) an alcohol;
(4) at least one amino acid present in an amount that is greater than zero and up to about 10 weight percent based on a total weight of said reagent composition; and; and
(5) iodine ($I_2$);
wherein a molar ratio of the derivative of imidazole to the sulfur dioxide or is greater than 1:1.

19. The reagent composition of claim 18 wherein said at least one amino acid is proline and is present in an amount of from about 0.2 to about 0.5 weight percent based on a total weight of said reagent composition.

20. The reagent composition of claim 18 wherein said sulfur dioxide is present in an amount of from about 0.05 to about 1, mols/liter of said reagent composition,
said derivative of imidazole is 2-ethylimidazole and is present is present in an amount of from about 0.5 to about 5, mols/liter of said reagent composition,
said at least one amino acid is proline and is present in an amount of from about 0.2 to about 0.5 weight percent based on a total weight of said reagent composition, and
said alcohol is methanol and/or ethanol.

* * * * *